US00PP25343P2

(12) United States Plant Patent
van der Meer et al.

(10) Patent No.: US PP25,343 P2
(45) Date of Patent: Mar. 10, 2015

(54) ALOE PLANT NAMED 'TIKI ZILLA'

(50) Latin Name: *Aloe hybrida*
Varietal Denomination: Tiki Zilla

(71) Applicants: Paulus A. M. van der Meer, Monster (NL); Adrianus L. M. van der Meer, Monster (NL)

(72) Inventors: Paulus A. M. van der Meer, Monster (NL); Adrianus L. M. van der Meer, Monster (NL)

( * ) Notice: Subject to any disclaimer, the term of this patent is extended or adjusted under 35 U.S.C. 154(b) by 125 days.

(21) Appl. No.: 13/815,655

(22) Filed: Mar. 13, 2013

(51) Int. Cl.
*A01H 5/00* (2006.01)

(52) U.S. Cl.
USPC ..... Plt./373

(58) Field of Classification Search
USPC ..... Plt./373
See application file for complete search history.

*Primary Examiner* — Susan McCormick Ewoldt
(74) *Attorney, Agent, or Firm* — C. A. Whealy

(57) ABSTRACT

A new and distinct cultivar of *Aloe* plant named 'Tiki Zilla', characterized by its compact and upright plant habit; leaves arranged in a dense basal rosette; green-colored leaves with greyed green-colored margins and spots; upright flowering stems; and good postproduction longevity.

3 Drawing Sheets

Botanical designation: *Aloe hybrida.*
Cultivar denomination: 'TIKI ZILLA'.

BACKGROUND OF THE INVENTION

The present Invention relates to a new and distinct cultivar of *Aloe* plant, botanically known as *Aloe hybrida* and hereinafter referred to by the name 'Tiki Zilla'.

The new *Aloe* plant is a product of a planned breeding program conducted by the Inventors in Monster, The Netherlands. The objective of the breeding program is to develop new stemless and thornless *Aloe* plants with attractive and unique leaves.

The new *Aloe* plant originated from a cross-pollination in April, 1997 of a proprietary selection of *Gasteria* sp.×(*Gasteria* sp.×*Aloe* sp.) identified as code number G17, not patented, as the female, or seed, parent with an unnamed proprietary selection of *Aloe saponaria*, not patented, as the male, or pollen, parent. The new *Aloe* plant was discovered and selected by the Inventors as a single flowering plant from within the resultant progeny of the cross-pollination in a controlled greenhouse environment in Monster, The Netherlands in October, 1999.

Asexual reproduction of the new *Aloe* plant by cuttings in a controlled greenhouse environment in Monster, The Netherlands since May, 2001 has shown that the unique features of this new *Aloe* plant are stable and reproduced true to type in successive generations.

SUMMARY OF THE INVENTION

Plants of the new *Aloe* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Tiki Zilla'. These characteristics in combination distinguish 'Tiki Zilla' as a new and distinct *Aloe* plant:

1. Compact and upright plant habit.
2. Leaves arranged in a dense basal rosette.
3. Green-colored leaves with greyed green-colored margins and spots.
4. Upright flowering stems.
5. Good postproduction longevity.

Plants of the new *Aloe* differ primarily from plants of the female parent selection primarily in the following characteristics:

1. Plants of the new *Aloe* had shorter leaves than plants of the female parent selection.
2. Leaf spots of plants of the new *Aloe* are larger than leaf spots of plants of the female parent selection.

Plants of the new *Aloe* differ primarily from plants of the male parent selection primarily in the following characteristics:

1. Plants of the new *Aloe* rarely produce thorns whereas plants of the male parent selection produce thorns.
2. Plants of the new *Aloe* have shorter leaves than plants of the male parent selection.

Plants of the new *Aloe* can be compared to plants of *Aloe* 'Cosmo', not patented. Plants of the new *Aloe* differ from plants of 'Cosmo' in the following characteristics:

1. Leaves of plants of the new *Aloe* are shorter than leaves of plants of 'Cosmo'.
2. Leaves of plants of the new *Aloe* have more distinct spots than leaves of plants of 'Cosmo'.

DESCRIPTION OF THE PHOTOGRAPHS

The accompanying colored photographs illustrate the overall appearance of the new *Aloe* plant showing the colors as true as it is reasonably possible to obtain in colored reproductions of this type. Colors in the photographs may differ slightly from the color values cited in the detailed botanical description which accurately describe the colors of the new *Aloe* plant.

The photograph on the first sheet comprises a side perspective view of a typical flowering plant of 'Tiki Zilla' grown in a container.

The photograph on the second sheet comprises a top perspective view of the leaves of a typical plant of 'Tiki Zilla'.

The photograph on the third sheet is a close-up view of a typical inflorescence of 'Tiki Zilla'.

DETAILED BOTANICAL DESCRIPTION

The aforementioned photographs and following observations and measurements describe plants that were grown during the winter in 12-cm containers in a glass-covered greenhouse in Monster, The Netherlands and under cultural practices typical of commercial *Aloe* production. During the production of the plants, day temperatures ranged from 17° C. to 21° C. and night temperatures ranged from 15° C. to 19° C. Plants were ten months and two years old when the description and photographs, respectively, were taken. In the following description, color references are made to The Royal Horticultural Society Colour Chart, 2007 Edition, except where general terms of ordinary dictionary significance are used.

Botanical classification: *Aloe hybrida* 'Tiki Zilla'.

Parentage:

*Female, or seed, parent*.—Proprietary selection of *Gasteria* sp.×(*Gasteria* sp.×*Aloe* sp.) identified as code number G17, not patented.

*Male, or pollen, parent*.—Unnamed selection of *Aloe saponaria*, not patented.

Propagation:

*Type*.—By cuttings.

*Time to initiate roots, summer*.—About 20 days at temperatures of 19° C. to 24° C.

*Time to initiate roots, winter*.—About 30 days at temperatures of 17° C. to 19° C.

*Root description*.—Medium in thickness, fleshy; white to brown in color.

*Rooting habit*.—Moderately freely branching; dense.

Plant description:

*Plant form and growth habit*.—Upright flowering plant; leaves arranged in a dense basal rosette; plants stemless; single erect flowering stem; low vigor.

*Plant height, soil level to top of flowers*.—About 74.3 cm.

*Plant height, soil level to top of foliar plane*.—About 13.1 cm.

*Plant diameter*.—About 19.9 cm.

*Leaves*.—Arrangement and quantity: Simple, arranged in a basal rosette, sessile; about 20 leaves per plant. Length: About 11.3 cm. Width: About 6.8 cm. Thickness: About 1.7 cm. Shape: Narrowly deltoid to broadly ovate. Apex: Broadly apiculate. Base: Broadly cuneate. Margin: Denticulate. Texture, upper and lower surfaces: Glabrous; succulent; spots and marginal teeth, muricate. Color: Developing leaves, upper surface: Close to between N137A and 147A (closest to darker than N137A); marginal teeth and spots, close to 191B to 191C. Developing leaves, lower surface: Close to N137A; spots, close to 191B to 191C. Fully opened leaves, upper surface: Close to between N137A and 147A (closest to darker than 147A); marginal teeth and spots, close to 191A to 191B. Fully opened leaves, lower surface: Close to N137A; spots, close to 191A to 191B.

Flower description:

*Flower shape and arrangement*.—Tubular flowers arranged in a terminal raceme; about 37 flowers develop per inflorescence; flowers face outwardly to slightly drooping.

*Fragrance*.—None detected.

*Natural flowering season*.—Plants flower from late winter into the spring in The Netherlands.

*Postproduction longevity*.—Flowers last about one week on the plant; flowers not persistent.

*Flower buds*.—Length: About 1.8 cm. Diameter: About 4 mm. Shape: Narrowly oblong, apex slightly curved upright. Color: Close to 35B; towards the apex, close to 137D.

*Inflorescence length*.—About 23 cm.

*Inflorescence width*.—About 7.5 cm.

*Flower diameter*.—About 8 mm.

*Flower length* (*height*).—About 2.9 cm.

*Perianth*.—Quantity and arrangement: Six tepals per flower; tepals fused towards the base; towards the apex, segments free, about 45% portion of the tepal. Tepal length: About 2.8 cm. Tepal width: About 3 mm. Tepal shape: Narrowly oblong. Tepal apex: Acute. Tepal margin: Entire. Tepal texture, upper and lower surfaces: Smooth, glabrous; velvety. Tepal color: When opening and fully opened, upper surface: Close to 31B to 31C; distally, close to 144A to 144C; margins, close to 155A; color becoming closer to 39A to 39B with development. When opening and fully opened, lower surface: Close to 35A to 35B; distally, close to between 143A and 144A to 144C; margins, close to 155A.

*Peduncles*.—Length: About 71 cm. Diameter: About 6 mm. Angle: Mostly erect to 15° from vertical. Strength: Moderately strong. Texture: Smooth, glabrous. Color: Close to 147A covered with a waxy cuticle, close to 194A.

*Pedicels*.—Length: About 1.1 cm. Diameter: About 0.15 mm. Angle: About 75° from vertical. Strength: Moderately strong. Texture: Smooth, glabrous. Color, upper surface: Close to 174A. Color, lower surface: Close to 144B.

*Reproductive organs*.—Stamens: Quantity per flower: Six. Filament length: About 2.4 cm. Filament color: Close to NN155B. Anther length: About 2 mm. Anther shape: Narrowly oblong. Anther color: Close to 28A. Pollen amount: Moderate. Pollen color: Close to 22B. Pistils: Quantity per flower: One. Pistil length: About 2.1 cm. Style length: About 2.05 mm. Style color: Close to 145C to 145D. Stigma shape: Pointed. Stigma color: Close to NN155C to NN155D. Ovary color: Close to 143A to 143B.

*Seeds and fruits*.—Seed and fruit development have not been observed on plants of the new *Aloe*.

Disease & pest resistance: Resistance to pathogens and pests common to *Aloe* plants has not been observed on plants of the new *Aloe*.

Temperature tolerance: Plants of the new *Aloe* have been observed to tolerate high temperatures of about 45° C. and to be hardy to USDA Hardiness Zone 10.

It is claimed:

1. A new and distinct *Aloe* plant named 'Tiki Zilla' as illustrated and described.

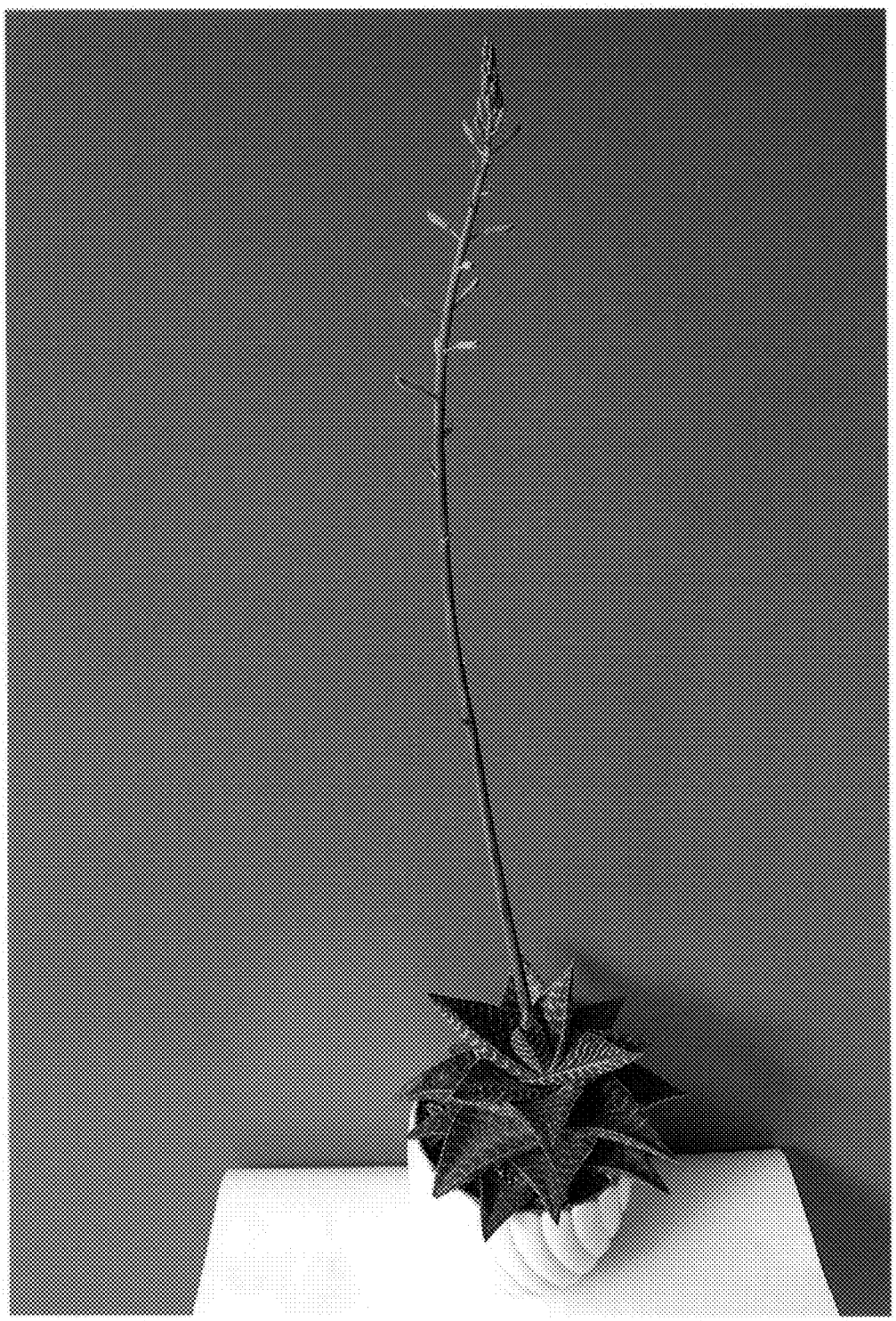

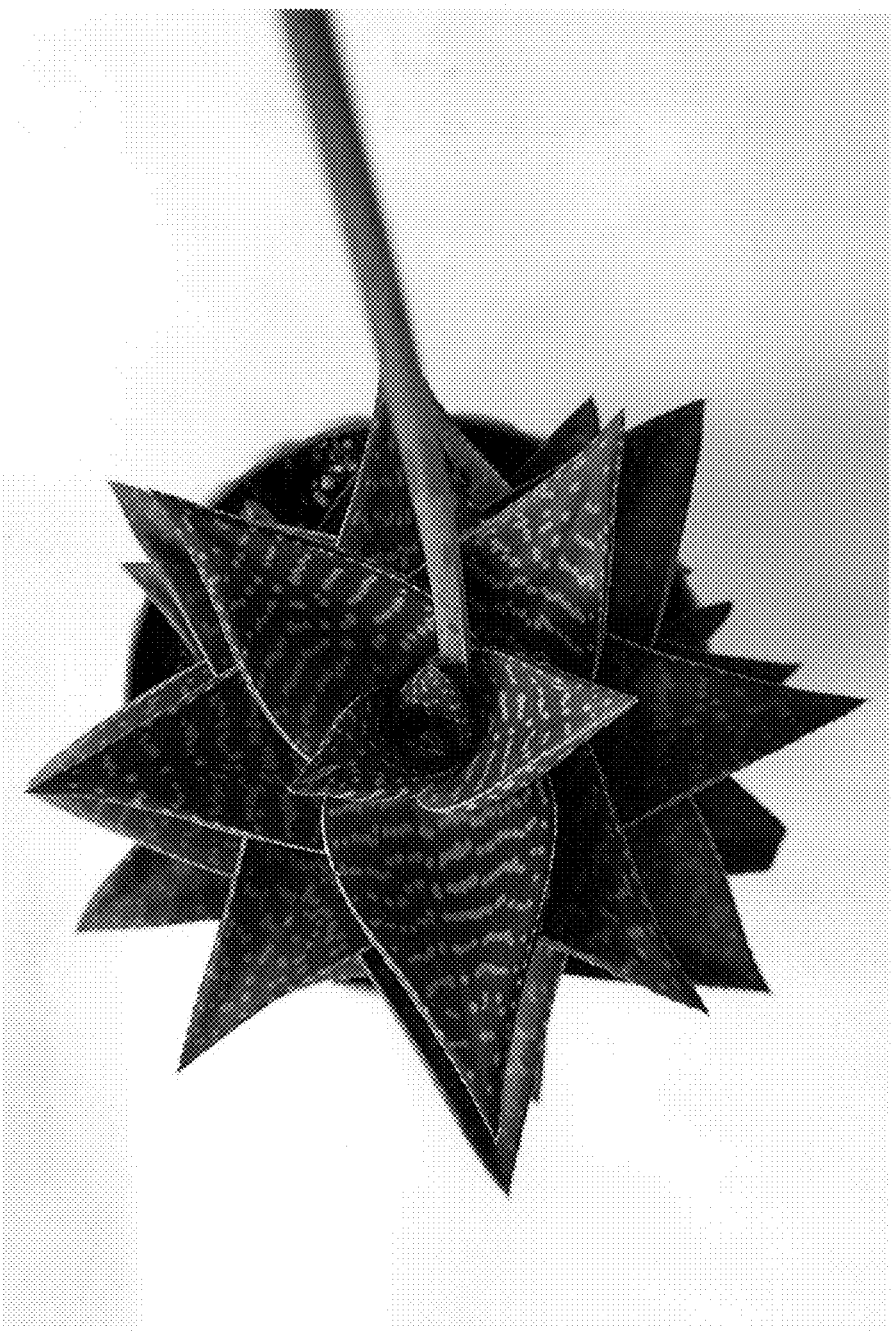

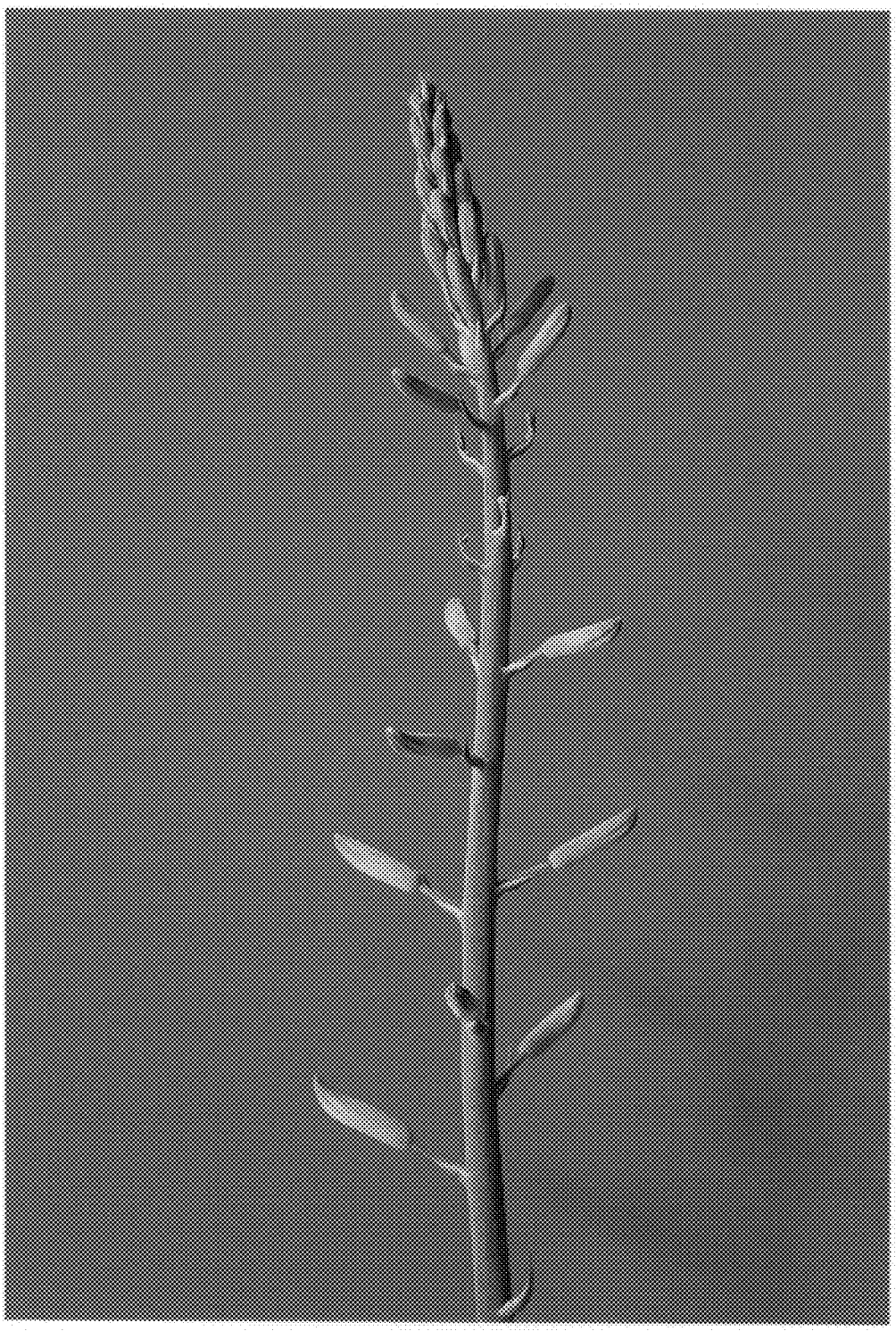

* * * * *